United States Patent [19]

Wu

[11] Patent Number: 5,536,870

[45] Date of Patent: Jul. 16, 1996

[54] PROCESS FOR PREPARING OLEFINS

[75] Inventor: Tse-Chong Wu, Baton Rouge, La.

[73] Assignee: Albemarle Corporation, Richmond, Va.

[21] Appl. No.: 390,466

[22] Filed: Feb. 17, 1995

[51] Int. Cl.$^6$ .......................... C07C 69/76; C07C 5/09; C07C 19/08; C07C 11/00

[52] U.S. Cl. .................. 560/56; 560/10; 560/15; 560/55; 560/103; 562/406; 585/435; 585/436; 568/658; 568/309; 570/128

[58] Field of Search .................. 562/406; 560/10, 560/15, 55, 103; 585/435, 436; 568/309, 658; 570/128

[56] References Cited

U.S. PATENT DOCUMENTS

| | | | |
|---|---|---|---|
| 4,246,164 | 1/1981 | Felder et al. | 260/501.17 |
| 5,225,603 | 7/1993 | Aslam et al. | 568/315 |
| 5,315,026 | 5/1994 | Wu | 560/105 |

FOREIGN PATENT DOCUMENTS 59-10545  1/1984  Japan .

OTHER PUBLICATIONS

R. F. Heck, *Palladium Reagents in Organic Syntheses*, Academic Press, 1985, pp. 276–291.
R. A. De Vries et al., *Organometallics*, vol. 13, No. 6, pp. 2405–2411 (1994).
W. Heitz et al., *Makromol. Chem.*, vol. 189, pp. 119–127 (1988).
K. Mori et al., *Bulletin of the Chemical Society of Japan*, vol. 46, pp. 1505–1508 (1973).
J. E. Plevyak et al., *J. Org. Chem.*, vol. 43, No. 12, pp. 2454–5456 (1978).
H. Alper et al., *J. Chem. Soc. Commun.*, 1983, pp. 1270–1271.
M. Aslam et al., *Synthesis*, No. 11, Nov. 1989, pp. 869–870.

*Primary Examiner*—Paul J. Killos
*Attorney, Agent, or Firm*—Philip M. Pippenger

[57] ABSTRACT

A process for preparing olefin compounds of the formula

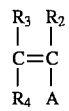

II where A is aryl, substituted aryl, heteroaryl, substituted heteroaryl, benzyl, substituted benzyl, vinyl or substituted vinyl and $R_2$, $R_3$ and $R_4$ are hydrogen, alkyl, cycloalkyl, alkyl-substituted cycloalkyl, aryl, substituted aryl, alkoxy, alkythio, heteroaryl, substituted heteroaryl, alkanoyl, aroyl, substituted aroyl, heteroarylcarbonyl, substituted heteroarylcarbonyl, trifluoromethyl or halo, which comprises reacting an organic halide of the formula A-X where X is chloro, bromo or iodo with a vinyl or substituted vinyl compound of the formula

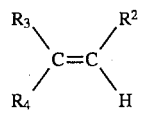

where $R_2$, $R_3$ and $R_4$ are as previously defined, in the presence of a catalytically effective amount of palladium or the salts of palladium, where palladium has a valence of 1 or 2 and a cyclic ligand of the formula

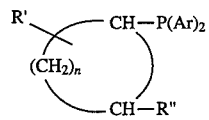

where R' is the same or different than R" and is hydrogen, alkyl or aryl either substituted or unsubstituted and Ar is phenyl, naphthyl, substituted phenyl or substituted naphthyl, substituted phenyl or substituted naphthyl and n is an integer from 3 to 6, to form an activated reaction mixture. Carboxylic acids can be prepared by carbonylation of such olefins.

62 Claims, No Drawings

PROCESS FOR PREPARING OLEFINS

FIELD OF THE INVENTION

The invention relates to a method for preparing substituted olefins by the palladium-catalyzed coupling of vinyl compounds with organic halides and to the subsequent preparation of carboxylic acids or esters.

BACKGROUND

The palladium-catalyzed vinylation of organic halides provides a very convenient method for forming carbon-carbon bonds at unsubstituted vinylic positions. The reaction, reported by Heck (*Palladium Reagents in Organic Syntheses,* Academic Press, Canada 1985) can be used to prepare fine organics, pharmaceuticals, and specialty monomers. For example, the reaction allows a one-step synthesis of substituted styrenes from aryl bromides and is an excellent method for preparation of a wide variety of styrene derivatives. Hertz et al., *Makromol Chem.,* 189, 119 (1968).

Vinyl toluenes have been reported as the product of a homogeneous palladium-catalyzed coupling of ethylene with bromotoluenes. R. A. DeVries et al., *Organometallics,* 13, 2405 (1994).

Arylation of propylene, ethylene, styrene, and methyl acrylate with iodobenzene was found to be catalyzed by metallic palladium in methanol to give methylstyrene, styrene, t-stilbene, and methyl cinnamate, respectively. Their yields and selectivities increased significantly by the addition of excess potassium acetate as an acceptor of hydriodic acid formed. Mori et al., *Bull. Chem. Soc., Japan,* 46, 1505 (1973).

A variety of styrene derivatives and 3-vinylpyridine were prepared in moderate to good yields by the palladium-tri-o-tolylphosphine catalyzed reaction of ethylene with aryl bromides or 3-bromopyridine, respectively. (Plevyak et al., *J. Org. Chem.* 43, 2454 (1978).

Alper et al. in *J. Chem Soc., Chem. Comm.,* 1270–1271, 1983, discloses the alkenes can react with carbon monoxide, water, hydrochloric acid and a mixture of palladium and copper to produce the hydrocarboxylated branched chain carboxylic acid. Oxygen is necessary to succeed in the reaction.

Another process for preparing the branched chain carboxylic acid ibuprofen is that of Japanese Patent Application (Kokai) No. 59-10545 (Mitsubishi Petrochemical, published January, 1984), which teaches that ibuprofen can be prepared by reacting p-isobutylstyrene with carbon monoxide and water or an alcohol in the presence of a palladium(II) catalyst and a peroxide, e.g., cumyl hydroperoxide.

A new process for preparing aryl substituted aliphatic carboxylic acids or their alkyl esters is disclosed in U.S. Pat. No. 5,315,026. A 1-aryl substituted olefin is reacted with carbon monoxide in the presence of water or an alcohol at a temperature between about 25° C. and about 200° C. A mixture useful as a catalyst is a palladium compound and a copper compound with at least one acid-stable ligand. Ligands which may be used include include monodentate or multidentate electron-donating substances such as those containing elements P, N, O and the like, and those containing multiple bonds such as olefinic compounds. Examples of such acid-stable ligands are trihydrocarbylphosphines, including trialkyl- and triarylphosphines, such as tri-n-butyl-, tricyclohexyl-, and triphenylphosphine; lower alkyl and aryl nitriles, such as benzonitrile and n-propionitrile; ligands containing pi-electrons, such as an allyl compound or 1,5-cyclooctadiene; piperidine, piperazine, trichlorostannate(II), and acetylacetonate; and the like.

One example of a suitable ligand is an acid-stable cyclic phosphine having the formula:

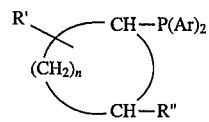

where R' is the same or different than R" and is hydrogen, alkyl or aryl, said aryl, either substituted or unsubstituted, and Ar is phenyl, naphthyl, substituted phenyl or substituted naphthyl and n is an integer from 3 to 6 is used as a catalyst. Together R', R" and the other carbon groups in the ring structure attached to phosphorous can form an aromatic ring, or naphthalene ring either substituted or unsubstituted so that the phosphine ligand can be $P(Ar)_3$ where the Ar is as defined above. Such ligands are generally known as triphenyl phosphine ligands. The term "trihydrocarbyl phosphine" is intended to mean ligands which contain one, two or three Ar groups. If less than three Ar groups are present, the balance (to provide a total of 3) is the cyclic group containing R' and R" as depicted in the formula.

DESCRIPTION OF THE PREFERRED EMBODIMENTS

Definitions

In the following specification, the meaning of the substituent groups is as follows: "alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl, and the like (for the purposes of this definition, "alkyl" may be replaced by "aliphatic". Such term includes "$C_1$ to $C_6$ alkyl" which is 1 to 6 linear or branched carbon atoms);

"cycloalkyl" means cyclic alkyl having 3 to 7 carbon atoms and includes cyclopropyl, cyclobutyl, cyclopentyl, cyclohexyl, cycloheptyl and the like;

"aryl" means phenyl, napthyl, or biphenyl;

"substituted aryl" means phenyl, naphthyl, or biphenyl substituted by at least one substituent selected from the group consisting of aroyl (as defined below), halogen (chlorine, bromine, fluorine or iodine), amino, nitro, hydroxy, alkyl, alkoxy (which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy), aryloxy including phenoxy and phenoxy substituted with halo, alkyl, alkoxy and the like, haloalkyl which means straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl and the like;

"alkyl-substituted cycloalkyl" means that the cycloalkyl moiety is cyclic alkyl having 3 to 7 carbon atoms and the alkyl moiety is straight or branched chain alkyl having 1 to 8 carbon atoms, and includes, for example, cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl, 6-cyclohexylhexyl and the like;

"alkylthio" means a divalent sulfur with alkyl occupying one of the valencies and includes the groups methylthio, ethylthio, propylthio, butylthio, pentylthio, hexylthio, octylthio and the like;

"heteroaryl" means 5 to 10 membered mono- or fused-heteroaromatic ring which has at least one heteroatom and includes those selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl; imidazolyl, pyrimidinyl, pyridazinyl, pyrazinyl, benzimidazolyl, quinolyl, oxazolyl, thiazolyl, indolyl and the like;

"substituted heteroaryl" means 5 to 10 membered mono- or fused-heteroaromatic ring which has at least one heteroaromatic selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus;

"alkanoyl" means alkanoyl having 2 to 18 carbon atoms and includes, for example, acetyl, propionyl, butyryl, isobutyryl, pivaloyl, valeryl, hexanoyl, octanoyl, lauroyl, stearoyl and the like;

"aroyl" means benzoyl or naphthoyl;

"substituted aroyl" means benzoyl or naphthoyl substituted by at least one substituent including those selected from the group consisting of halogen, amino, nitro, hydroxy, alkyl, alkoxy and haloalkyl on the benzene or naphthalene ring;

"heteroarylcarbonyl" means that the heteroaryl moiety is 5 to 10 membered mono- or fused-heteroaromatic ring having at least one heteroatom selected from the group consisting of nitrogen, oxygen and sulfur as mentioned above, and includes, for example, furoyl, thinoyl, nicotinoyl, isonicotinoyl, pyrazolylcarbonyl, imidazolylcarbonyl, pyrimidinylcarbonyl, benzimidazolylcarbonyl and the like;

"substituted heteroarylcarbonyl" means the above-mentioned heteroarylcarbonyl which is substituted by at least one substituent selected from the group consisting of halogen, amino, nitro, hydroxy, alkyl, alkoxy and haloalkyl on the heteroaryl nucleus; and includes, for example, 2-oxo-1,3-dioxolan-4-ylmethyl, 2-oxo-1,3-dioxan-5-yl and the like;

"vinyl" means an unsaturated substituent having at least one unsaturated double bond and having the formula $CH_2=CH-$;

"substituted vinyl" means the above vinyl substituent having at least one of the protons on the terminal carbon atom replaced with alkyl, cycloalkyl, alkyl-substituted cycloalkyl, aryl, substituted aryl, heteroaryl or substituted heteroaryl.

In one embodiment of the present invention, olefin compounds are produced having the formula:

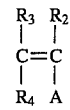

where $R_2$, $R_3$ and $R_4$ are the same or different and are individually hydrogen, alkyl, cycloalkyl, alkyl-substituted cycloalkyl, aryl either substituted or unsubstituted, alkoxy, alkylthio, heteroaryl either substituted or unsubstituted, alkanoyl, aroyl either substituted or unsubstituted, heteroarylcarbonyl either substituted or unsubstituted, trifluoromethyl or halo, and A is aryl, substituted aryl, heteroaryl, substituted heteroaryl, benzyl, substituted benzyl, vinyl or substituted vinyl.

Preferably, in the compounds of Formula II, A is unsubstituted or substituted aryl, $R_2$, $R_3$ and $R_4$ are hydrogen, $C_1$ to $C_6$ alkyl, substituted or unsubstituted phenyl or trifluoromethyl.

Most preferably A is phenyl substituted with alkyl (e.g., isobutyl) or naphthyl substituted with alkoxy (e.g., methoxy), $R_2$, $R_3$ and $R_4$ are hydrogen, methyl or trifluoromethyl, especially hydrogen.

The compounds of Formula II are produced by the reaction of an organic halide of the Formula A-X where X is chloro, bromo, iodo, diazonium, triflate, or other leaving groups which can be found in organic textbooks, and A is as previously defined, with a vinyl or substituted vinyl compound of the formula

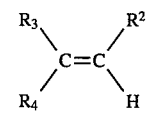

where $R_2$, $R_3$ and $R_4$ are as previously defined.

The reaction, sometimes called a "vinylation" reaction, is typically carried out in the presence of a reaction promoting catalyst that is palladium metal or a palladium compound in which the palladium has a valence of zero, 1 or 2 and a cyclic ligand of the formula

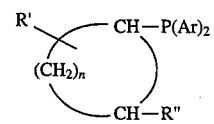

where R' and R" are the same or different and are individually hydrogen, alkyl, aryl or substituted aryl, Ar is phenyl, naphthyl, substituted phenyl or substituted naphthyl and n is an integer from 3 to 6. Preferably, R' and R" are the same or different and are $C_1$ to $C_6$ alkyl, Ar is phenyl or naphthyl and n is 3 or 4. Most preferably, R' is methyl or ethyl, R" is $C_1$ to $C_6$ branched alkyl, Ar is phenyl and n is 4. Especially preferred is neomenthyldiphenylphosphine as the cyclic ligand.

The vinylation reaction is carried out in the presence or in the absence of a solvent. When a solvent is used, it can be a polar solvent such as, for example, acetonitrile, tetrahydrofuran, dioxane, or dimethylformamide.

Conditions for the vinylation reaction usually require an equimolar ratio of organic halide to vinyl or substituted vinyl compound, although an excess of vinyl compound is preferred. The catalyst/ligand are typically used at about a ratio of 1 mol of organic halide to 0.0005 mol of palladium or palladium compound. The cyclic ligand is present in the same or higher molar proportion as the metal or metal compound. It should be noted that levels of palladium metal or palladium compound and ligand can be substantially higher (up to 10 times). When relatively inactive species of vinyl or halide are encountered, for example, highly substituted olefins and/or organic halides bearing strongly electron donating substituents may require these higher amounts of catalyst/ligand.

Temperatures of reaction are quite modest, varying from about 25° C. to 200° C. (preferably 60° C. to 150° C.) with pressures (for the gaseous vinyl compounds) being from atmospheric up to about 3000 psi (preferably 400 to 1000 psi). With the improved catalyst combination of the present invention, reaction times are unusually short, typically giving complete reaction in from 1 to 24 hours, typically 2 to 4 hours. Higher temperatures and pressures tend to cause decomposition of the olefin reactants and products and this should be avoided.

The olefin formed in the reaction mixture is readily separated by conventional means, e.g., distillation or extraction with a non-polar solvent, e.g., liquid hydrocarbons like hexane having from 5 to 12 carbon atoms, both linear and branched.

A further embodiment of the present invention is one in which the olefin compound of Formula II can be used with or without isolation (preferably without isolation) from the reaction mixture in the catalytic carboxylation step to produce compounds of Formula III

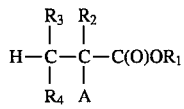

where $R_1$, $R_2$, $R_3$, $R_4$ and A are as previously defined.

The catalytic carboxylation of the compound of Formula II is conducted, at a temperature between about 25° C. and about 200° C., preferably about 25°–120° C., and most preferably about 25°–100° C. Higher temperatures can also be used. It has been found that a small advantage in yield is obtained by gradually increasing the temperature within the preferred ranges during the course of the reaction.

The partial pressure of carbon monoxide in the reaction vessel is at least about 1 atmosphere (0 psig) at ambient temperature (or the temperature at which the vessel is charged). Any higher pressures of carbon monoxide can be used up to the pressure limits of the reaction apparatus. A pressure up to about 3000 psig is convenient in the process. More preferred is a pressure from 0 to about 3000 psig at the reaction temperature and most preferred is a pressure from 0 to about 1000 psig. It should be noted that the presence of oxygen is undesirable in the hydrocarboxylation reaction of this invention. Hence, an atmosphere of 100% carbon monoxide is most preferred to carry out this process. Various inert gases can, however, be incorporated in the reaction mass (nitrogen, argon, etc.) the only criteria being that the process should not be slowed to the point of requiring exceptionally long periods to complete the reaction.

The carboxylation is conducted in the presence of at least about one mol of water or aliphatic alcohol per mol of the compound of Formula II; however, an excess is preferred in order to assist in driving the reaction to completion. Although there is no real upper limit to the amount of water or alcohol except that imposed by practicality (e.g. the size of the reaction vessel), an amount up to about 100 mols per mol of the compounds of Formula II is useful in the process. Further, controlling the amount of water or alcohol used in the process of this invention is advantageous in terms of producing the highest yields. Therefore, an amount from about 1 to about 50 mols of water or alcohol per mol of the compounds of Formula II is preferred, and an amount from about 2 to about 24 mols of water or alcohol per mol of the such olefinic compound is most preferred. The product of the reaction is a carboxylic acid (where $R_1$ is hydrogen) or carboxylic acid ester (where $R_1$ is alkyl) of Formula III.

The present invention embraces any racemates and individual optical isomers of the compounds of Formula III having a chiral carbon atom. For example, when compounds of Formula III wherein the acid is 2-(6-methoxy-2-naphthyl)propionic acid, are subjected to resolution as taught in U.S. Pat. No. 4,246,164 (incorporated herein by reference), the analgesic compound naproxen is produced.

Any alcohol which produces an ester of the carboxylic acid may be used in the practice of this invention. In a preferred embodiment, the $C_1$ to $C_6$ aliphatic alcohols are used. Examples of the alcohols to be used in this embodiment include methyl alcohol, ethyl alcohol, n-propyl alcohol, isopropyl alcohol, n-, iso-, sec-, and tert-butyl alcohols, the pentyl alcohols, (isoamyl alcohol, especially to form the naproxen ester), the hexyl alcohols, etc. Methyl alcohol is highly preferred, and ethyl alcohol is most highly preferred. Other alcohols, glycols, or aromatic hydroxy compounds may also be used. In the broadest sense, these alcohols provide a source of alkoxide ions for this reaction. However, any other "source of alkoxide ions" may also be used. The source of such alkoxide ions is from a compound selected from the group consisting of $HC(OR_1)_3$, $(R)_2C(OR_1)_2$, $HC(O)OR_1$, $B(OR_1)_3$, $Ti(OR_1)_4$ and $Al(OR_1)_3$ where R is hydrogen or individually the same or different than $R_1$ and $R_1$ is as previously defined.

In a preferred embodiment of this invention, the carboxylation reaction is initiated under neutral conditions, i.e., with no added acid. It can also be performed in the presence of an added acid. When acids are added, such acids include sulfuric acid, phosphoric acid or sulfonic acids. A hydrogen halide acid such as hydrochloric or hydrobromic acid is preferred. The hydrogen halide may be added as a gas phase or as a liquid phase. Any concentration may be used. Hydrochloric acid is particularly preferred, at a concentration up to about 10%; more highly preferred is a concentration from about 10% to about 30%. The amount of acid added is such as to provide up to about 40 mols of hydrogen ion per mol of compound of Formula II; more preferred is an amount to provide up to about 10 mols of hydrogen ion per mol of compound; the most preferred amount provides up to about 4 mols of hydrogen ion per mol of the compounds of Formula II.

The catalytic carboxylation process of this invention is conducted in the presence of a reaction-promoting quantity of (i) palladium metal or a palladium compound in which the palladium has a valence of zero, 1 or 2, or (ii) a mixture of a palladium metal or palladium compound and a copper compound, with (iii) the cyclic ligand of Formula I. The compounds of palladium and copper are sometimes referred to as palladium and copper salts.

In one embodiment, palladium and copper compounds are inorganic salts and are added as a preformed complex of, for example, palladium(II) chloride or bromide, copper(II) chloride or bromide and carbon monoxide or any other similar complex. In a preferred embodiment, active catalytic species are formed in situ by the addition to the reaction mixture of the individual components, i.e., a ligand, a copper compound, and a palladium compound such as the inorganic salts of palladium(II) and copper(II). These inorganic salts include the chlorides, bromides, nitrates, sulfates, or acetates. In the most preferred embodiment, neomenthyldiphenylphosphine, copper(II) chloride, and palladium(II) chloride are used and are added individually or together, either simultaneously or sequentially.

The palladium metal or the palladium compound or the mixture of palladium and copper compounds can be supported on carbon, silica, alumina, zeolite, clay and other polymeric materials and used as the heterogeneous catalysts.

The amount of the mixture of copper and palladium compounds or of palladium metal or its compounds preferably employed is such as to provide from about 4 to about 8000 mols of the compound of Formula II per mol of the mixture of metal or metal salt; more preferred is an amount to provide from about 20 to 2000 mols of the compounds of Formula II per mol of the metal salt mixture. The process of this invention is conducted in the presence of at least one mol of the cyclic ligand per mol of the mixture of the metal or metal salts. More preferably, about 1 to about 40 mols of ligand per mol of the mixture are present, and most preferably about 1 to about 20 mols of ligand per mol of the mixture are used.

The presence of a solvent is not required in the process of this invention, although it may be desirable in some circumstances. Those solvents which can be used include one or more of the following: ketones, for example, acetone, methyl ethyl ketone, diethyl ketone, methyl n-propyl ketone, acetophenone, and the like; linear, poly and cyclic ethers, for example, diethyl ether, di-n-propyl ether, di-n-butyl ether, ethyl n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethyl benzene, xylenes, and similar compounds. Alcohols are also suitable as solvents, for example, methanol, ethanol, 1-propanol, 2-propanol isomers of butanol, isomers of pentanol, etc. Acids and esters may also be used, such as formic or acetic acid or ethyl acetate etc. When as ester or an alcohol is used as solvent, the product is the corresponding ester of the carboxylic acid. Most highly preferred are ethers, especially tetrahydrofuran. When solvents are used, the amount can be up to about 100 mL per gram of the compounds of Formula II, but the process is most advantageously conducted in the presence of about 1 to 30 mL per gram of the compound of Formula II.

In those specific embodiments of this invention in which an ester is produced, e.g. ibuprofen alkyl ester, the ester may be conveniently converted to the acid (ibuprofen itself) by conventional methods of hydrolysis. Base hydrolysis can also be employed if desired to produce pharmaceutically acceptable salts wherein the cation is sodium, potassium, calcium, hydrogen carbonate or a quaternary ammonium compound.

Examples of compounds produced by use of the invention include ibuprofen; 2-(6-methoxy-2-naphthyl)propionic acid; 2-(3-fluoro-4-biphenylyl)propionic acid (also known as flurbiprofen) and 2-(3-benzoylphenyl)propionic acid (also known as ketoprofen). As described herein the bromo precursor of each of the above compounds is reacted with ethylene in this presence of a base (e.g., triethyl amine) and a palladium catalyst (as described herein, including a ligand such as neomenthyldiphenylphosphine). The base should be selected to avoid beta hydride elimination under reaction conditions and should not react with the olefin or bromo precursor to any appreciable extent. The bromo precursor substitutes on the ethylene to provide the substituted olefin which is then carboxylated (using carbon monoxide and palladium catalyst as described herein) to produce the corresponding acid product (if water forms part or all of the solvent system) or the corresponding ester (if an alcohol such as methyl, ethyl or isoamyl alcohol) is used as all or part of the solvent.

The above reactions can be exemplified as follows:

IBUPROFEN

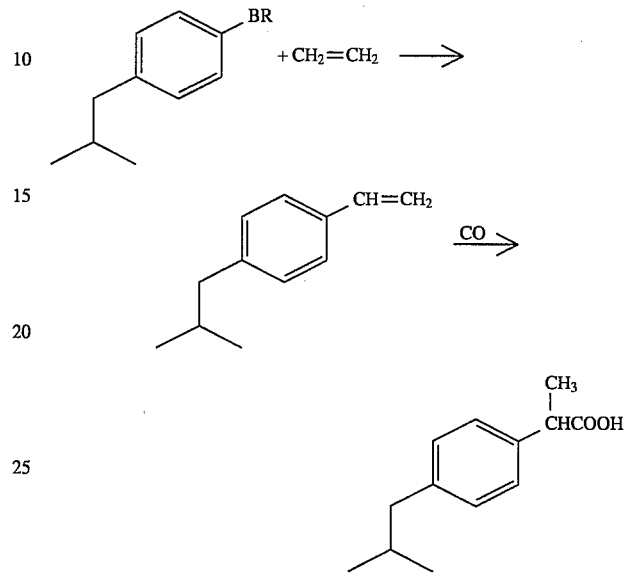

FLURBIPROFEN:

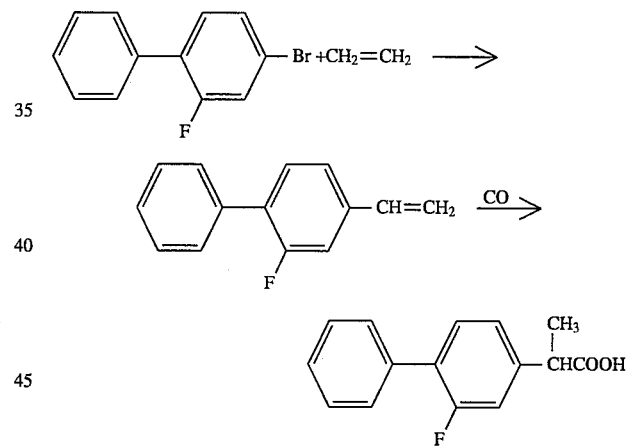

KETOPROFEN:

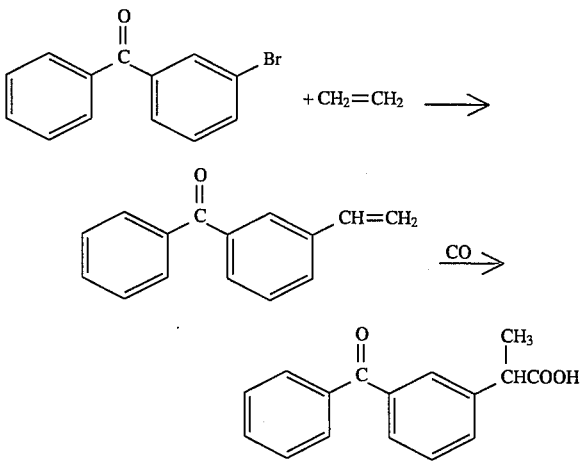

NAPROXEN:

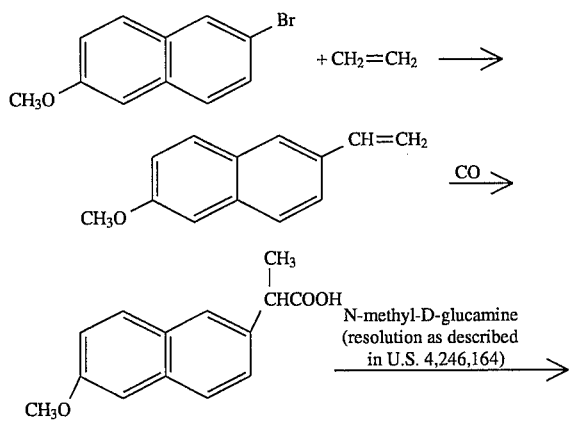

FENOPROFEN:

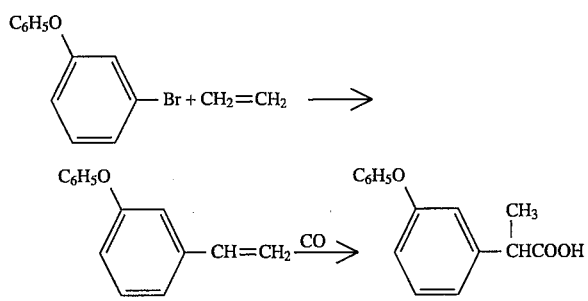

In the above reactions the ethylene pressure should be 50 to 3000 psi (preferably 400 to 1000 psi), the temperature is 30° C. to 200° C. (preferably 60° C. to 150° C.). Temperatures and pressures are selected to minimize olefin decomposition. Palladium$^{(+2)}$ is used in the form of its salts (e.g., acetate or chloride) along with a ligand as described with the phosphine ligands being preferred.

The bromo precursors are frequently commercially available and/or can be readily prepared by those skilled in the art. For example, Aldrich Chemical Company sells m-bromophenol and m-bromoanisole while Albemarle PPC (Paris, France) sells 6-methoxy-2-bromonaphthalene. The bromo precursors of ibuprofen can be prepared by bromination using standard Friedel-Crafts catalysts (e.g., zinc bromide or ferric bromide). The bromo precursor of ketoprofen can be prepared by bromination of methyl benzoate (or a similar lower hydrocarbon ester) using aluminum chloride followed by NaOH hydrolysis, conversion to the acid chloride (e.g., with $SOCl_2$) and reaction with benzene (again, using a Friedel-Crafts catalyst such as $AlCl_3$).

In addition to the profen compounds described above, other profen compounds which can be prepared by use of this invention to convert the corresponding bromo precursors by reaction with ethylene include protizinic acid, tiaprofenic acid, indoprofen, benoxaprofen, carprofen, pirprofen, pranoprofen, alminoprofen, suprofen and loxoprofen.

The follow examples are given to illustrate the process of this invention and are not intended as a limitation thereof.

EXAMPLES

NMDP=Neomenthyldiphenylphosphine
IBS=4-Isobutylstyrene
BIBB=4-Bromoisobutylbenzene
DIBE=1,1-Bis(4-isobutylphenyl)ethylene
DIBS=4,4'-Diisobutylstilbene

Example 1

$Pd(OAc)_2$ (11.0 mg, 0.0490 mmol) and NMDP (0.100 g, 0.308 mmol) were loaded to an autoclave (Hastelloy C, 100 mL) in a dry box. The reactor was assembled in the dry box and set up in the hood. $CH_3CN$ (12.5 mL), $Et_3N$ (12.5 mL) and BIBB (10.6 g, 49.7 mmol) were added via syringe. The reactor was purged with ethylene (2×150 psig) and then filled with ethylene (280 psig). The mixture was stirred at 120°–125° C. for 2 h. GC analysis of an aliquot showed IBS (95.5 area %), DIBE (0.6%), and DIBS (4.0%).

Example 2

$Pd(OAc)_2$ (11.0 mg, 0.0490 mmol) and NMDP (0.100 g, 0.308 mmol) were loaded to an autoclave (Hastelloy B, 100 mL) in a dry box. The reactor was assembled in the dry box and set up in the hood. $CH_3CN$ (12.5 mL), $Et_3N$ (12.5 mL) and BIBB (10.6 g, 49.7 mmol) were added via syringe. The reactor was purged with ethylene (2×150 psig) and then filled with ethylene (320 psig). The mixture was stirred at 100°–105° C. for 2 h. GC analysis of an aliquot showed IBS (97.6 area %), DIBE (0.1%), and DIBS (2.4%).

Example 3

$Pd(OAc)_2$ (11.0 mg, 0.0490 mmol) and NMDP (0.100 g, 0.308 mmol) were loaded to an autoclave (Hastelloy C, 100 mL) in a dry box. The reactor was assembled in the dry box and set up in the hood. $CH_3CN$ (12.5 mL), $Et_3N$ (12.5 mL) and BIBB (10.6 g, 49.7 mmol) were added via syringe. The reactor was purged with ethylene (2×150 psig) and then filled with ethylene (330 psig). The mixture was stirred at 80°–85° C. for 4 h. GC analysis of an aliquot showed IBS (97.9 area %) and DIBS (2.0%).

Example 4 (Comparative)

$Pd(OAc)_2$ (11.0 mg, 0.0490 mmol) and $(o-Tol)_3P$ (94.0 mg, 0.309 mmol) were loaded to an autoclave (Hastelloy B, 100 mL) in a dry box. The reactor was assembled in the dry box and set up in the hood. $CH_3CN$ (12.5 mL), $Et_3^N$ (12.5 mL) and BIBB (10.6 g, 49.7 mmol) were added via syringe. The reactor was purged with ethylene (2×150 psig) and then filled with ethylene (330 psig). The mixture was stirred at 80°–85° C. for 8 h. GC analysis of an aliquot showed IBS (24.0 area %), BIBB (76.0%), and DIBS (trace).

Example 5

$Pd(OAc(_2$ (11.0 mg, 0.0490 mmol) and $(Cyclohexyl)_3P$ (87.0 mg, 0.310 mmol) were loaded to an autoclave (Hastelloy B, 100 mL) in a dry box. The reactor was assembled in the dry box and set up in the hood. $CH_3CN$ (12.5 mL), $Et_3N$ (12.5 mL) and BIBB (10.6 g, 49.7 mmol) were added via syringe. The reactor was purged with ethylene (2×150 psig) and then filled with ethylene (300 psig). The mixture was stirred at 80°–85° C. for 8 h. GC analysis of an aliquot showed no reaction.

Example 6 (Comparative)

$Pd(OAc)_2$ (11.0 mg, 0.0490 mmol) and $Ph_3P$ (81.0 mg, 0.309 mmol) were loaded to an autoclave (Hastelloy B, 100 mL) in a dry box. The reactor was assembled in the dry box and set up in the hood. $CH_3CN$ (12.5 mL), $Et_3N$ (12.5 mL)

and BIBB (10.6 g, 49.7 mmol) were added via syringe. The reactor was purged with ethylene (2×150 psig) and then filled with ethylene (320 psig). The mixture was stirred at 80°–85° C. and monitored by GC. GC analysis of an aliquot in 8 h showed IBS (14.4 GC area %), BIBB (84.6%), and DIBS (trace).

Example 7

Pd(OAc)$_2$ (5.0 mg, 0.022 mmol) and NMDP (45 mg, 0.14 mmol) were loaded to an autoclave (Hastelloy B, 100 mL) in a dry box. The reactor was assembled in the dry box and set up in the hood. CH$_3$CN (14 mL), Et$_3$N (14 mL) and BIBB (11.8 g, 55 mmol) were added via syringe. The reactor was purged with ethylene (2×150 psig) and then filled with ethylene (280 psig). The mixture was stirred at 100°–105° C. for 4 h. GC analysis of an aliquot showed IBS (97.8 area %) and dimers (2.2%).

Example 8

PdCl$_2$ (9.0 mg, 0.0510 mmol) and NMDP (0.100 g, 0.308 mmol) were loaded to an autoclave (Hastelloy C, 100 mL) in a dry box. The reactor was assembled in the dry box and set up in the hood. CH$_3$CN (12.5 mL), Et$_3$N (12.5 mL) and BIBB (10.7 g, 50.2 mmol) were added via syringe. The reactor was purged with ethylene (2×150 psig) and then filled with ethylene (300 psig). The mixture was stirred at 80°–85° C. for 4 h. GC analysis of an aliquot showed IBS (98.2 area %), DIBE (0.1%), and DIBS (1.6%).

Example 9

PdCl$_2$ (9.0 mg, 0.0510 mmol), NMDP (0.100 g, 0.308 mmol), and CaO (1.5 g, 26.7 mmol) were loaded to an autoclave (Hastelloy C, 100 mL) in a dry box. The reactor was assembled in the dry box and set up in the hood. DMF (30 mL) and BIBB (10.6 g, 49.7 mmol) were added via syringe. The reactor was purged with ethylene (2×150 psig) and then filled with ethylene (360 psig). The mixture was stirred at 80°–85° C. for 6 h. GC analysis of an aliquot showed IBS (95.9 area %), BIBB (2.0%), DIBE (0.1%), and DIBS (2.1%).

Example 10

PdCl$_2$ (9.0 mg, 0.0510 mmol) and NMDP (0.100 g, 0.308 mmol) were loaded to an autoclave (Hastelloy C, 100 mL) in a dry box. The reactor was assembled in the dry box and set up in the hood. DMF (20 mL), Et$_3$N (7.5 mL) and BIBB (10.7 g, 50.2 mmol) were added via syringe. The reactor was purged with ethylene (2×150 psig) and then filled with ethylene (300 psig). The mixture was heated to 80°–85° C. and the reactor was pressurized to 520 psig with ethylene. The mixture was stirred at this temperature for 2.5 h. GC analysis of an aliquot showed IBS (97.5 area %), DIBE (0.1%), and DIBS (2.5%).

Example 11

PdCl$_2$ (7.0 mg, 0.0395 mmol) and NMDP (0.130 g, 0.401 mmol) were loaded to an autoclave (Hastelloy C, 100 mL) in a dry box. The reactor was assembled in the dry box and set up in the hood. DMF (15 mL), Et$_3$N (10.2 g), and BIBB (21.0 g, 98.5 mmol) were added via syringe. The reactor was purged with ethylene (2×150 psig) and then filled with ethylene (300 psig). The mixture was stirred at 120° C. for 1 h. GC analysis of an aliquot showed IBS (92.0 area %), BIBB (0.4%), DIBE (0.7%), and DIBS (6.9%).

Example 12

Pd(OAc)$_2$ (11.0 mg, 0.0490 mmol), NMDP (0.100 g, 0.308 mmol), and 2-bromo-6-methoxynaphthalene (11.8 g, 49.8 mmol) were loaded to an autoclave (Hastelloy B, 100 mL) in a dry box. The reactor was assembled in the dry box and set up in the hood. CH$_3$CN (20 mL) and Et$_3$N (8 mL) were added via syringe. The reactor was purged with ethylene (2×150 psig) and then filled with ethylene (320 psig). The mixture was stirred at 80°–85° C. for 5 h. GC analysis showed only 2-methoxy-6-vinylnaphthalene. The reaction mixture was cooled to room temperature and ethylene pressure was released. The mixture was filtered and the precipitate was washed with CH$_2$Cl$_2$ (150 mL). The combined filtrate was washed with HCl (1N, 2×50 mL), H$_2$O (50 mL), and brine (50 mL). The organic layer was dried (Na$_2$SO$_4$) and concentrated under reduced pressure to give a white solid (8.76 g, 96%): mp=92°–93° C.

What is claimed is:

1. A process for preparing an aryl-substituted aliphatic carboxylic acid or ester or salts thereof having the formula

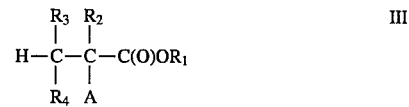

where R$_1$ is hydrogen or alkyl, R$_2$, R$_3$ and R$_4$ are hydrogen, alkyl, cycloalkyl, alkyl-substituted cycloalkyl, aryl either substituted or unsubstituted, alkoxy, alkylthio, heteroaryl either substituted or unsubstituted, heteroarylcarbonyl either substituted or unsubstituted, trifluoromethyl or halo and A is unsubstituted or substituted aryl or heteroaryl which comprises (i) reacting an aromatic halide of the formula A-X where X is chloro, bromo, iodo, or diazonium and A is as previously described, with an olefinic compound of the formula

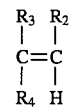

where R$_2$, R$_3$ and R$_4$ are as previously described, in the presence of a catalyst that is (a) palladium(O) or the salts of palladium having a valence of zero, 1 or 2 or a mixture of said palladium(O) or said salts of palladium and the salts of copper, and (b) a ligand of the formula:

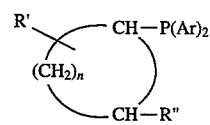

where R' is the same or different than R" and is hydrogen, alkyl or aryl either substituted or unsubstituted and Ar is phenyl, naphthyl, substituted phenyl or substituted naphthyl, substituted phenyl or substituted naphthyl and n is an integer from 3 to 6, to form an activated reaction mixture; and (ii) treating said activated reaction mixture with carbon monoxide at a pressure of at least 1 atmosphere and a temperature of from about 25° C. to about 200° C.

2. The process according to claim 1 wherein A is unsubstituted or substituted aryl, R$_2$, R$_3$ and R$_4$ are hydrogen, C$_1$ to C$_6$ alkyl, substituted or unsubstituted phenyl or trifluoromethyl.

3. The process according to claim 2 wherein A is phenyl substituted with alkyl, phenyl, benzoyl or phenoxy, or naphthyl substituted with alkoxy and $R_2$, $R_3$ and $R_4$ are hydrogen, methyl or trifluoromethyl.

4. The process according to claim 3 wherein A is phenyl substituted with isobutyl and $R_2$, $R_3$ and $R_4$ are hydrogen.

5. The process according to claim 3 where A is naphthyl substituted with methoxy and $R_2$, $R_3$ and $R_4$ are hydrogen.

6. The process according to claim 3 where A is biphenyl substituted at the 3 position with fluorine and $R_2$, $R_3$ and $R_4$ are hydrogen.

7. The process according to claim 3 where A is 3-phenoxyphenyl and $R_2$, $R_3$, and $R_4$ are hydrogen.

8. The process according to claim 3 where A is 3-benzoylphenyl and $R_2$, $R_3$ and $R_4$ are hydrogen.

9. The process according to claim 1 wherein said catalyst is (i) a salt of palladium having a valence of 2, and (ii) said ligand is neomenthyldiphenylphosphine.

10. A process for preparing an olefinic compound of the formula

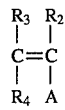
                II where A is aryl, substituted aryl, heteroaryl, substituted heteroaryl, benzyl, substituted benzyl, vinyl or substituted vinyl and $R_2$, $R_3$ and $R_4$ are hydrogen, alkyl, cycloalkyl, alkyl-substituted cycloalkyl, aryl, substituted aryl, alkoxy, alkythio, heteroaryl, substituted heteroaryl, alkanoyl, aroyl, substituted aroyl, heteroaryl-carbonyl, substituted heteroarylcarbonyl, trifluoromethyl or halo, which comprises reacting an organic halide of the formula A-X where X is chloro, bromo, iodo, or diazonium with a vinyl or substituted vinyl compound of the formula

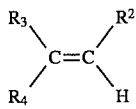

where $R_2$, $R_3$ and $R_4$ are as previously defined, in the presence of a catalytically effective amount of palladium or the salts of palladium, where palladium has a valence of 1 or 2 and a cyclic ligand of the formula

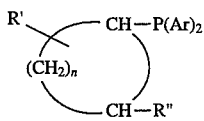

where R' is the same or different than R" and is hydrogen, alkyl or aryl either substituted or unsubstituted and Ar is phenyl, naphthyl, substituted phenyl or substituted naphthyl, substituted phenyl or substituted naphthyl and n is an integer from 3 to 6, to form an activated reaction mixture containing substantial amounts of the olefin described above.

11. The process according to claim 10 wherein A is unsubstituted or substituted aryl, $R_2$, $R_3$ and $R_4$ are hydrogen, $C_1$ to $C_6$ alkyl, substituted or unsubstituted phenyl or trifluoromethyl.

12. The process according to claim 11 wherein A is phenyl substituted with alkyl or naphthyl substituted with alkoxy and $R_2$, $R_3$ and $R_4$ are hydrogen, methyl or trifluoromethyl.

13. The process according to claim 12 wherein A is phenyl substituted with isobutyl and $R_2$, $R_3$ and $R_4$ are hydrogen.

14. The process according to claim 12 where A is naphthyl substituted with methoxy and $R_2$, $R_3$ and $R_4$ are hydrogen.

15. The process according to claim 11 wherein X is bromo.

16. The process according to claim 11 wherein A is phenyl substituted with isobutyl and $R_2$, $R_3$ and $R_4$ are hydrogen.

17. The process according to claim 11 wherein A is naphthyl substituted with methoxy and $R_2$, $R_3$ and $R_4$ are hydrogen.

18. The process according to claim 11 wherein A is biphenyl substituted at the 3 position with fluorine and $R_2$, $R_3$ and $R_4$ are hydrogen.

19. The process according to claim 11 wherein A is 3-phenoxyphenyl and $R_2$, $R_3$, and $R_4$ are hydrogen.

20. The process according to claim 11 wherein A is 3-benzoylphenyl and $R_2$, $R_3$ and $R_4$ are hydrogen.

21. The process according to claim 10 wherein said catalyst is (i) a salt of palladium having a valence of 2, and ii) said ligand is neomenthyldiphenylphosphine.

22. The process according to claim 10 including the step of isolating the olefin from the activated reaction mixture.

23. A process for preparing an aryl-substituted olefin having the formula

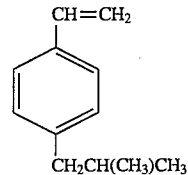

which comprises
(i) reacting an aromatic halide of the formula A-X where X is chloro, bromo, iodo, or diazonium and A is p-isobutylphenyl with ethylene in the presence of a catalytically effective amount of palladium or the salts of palladium, where palladium has a valence of 1 or 2 and a cyclic ligand of the formula

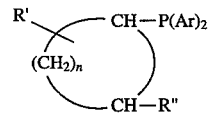

where R' is the same or different than R" and is hydrogen, alkyl or aryl either substituted or unsubstituted and Ar is phenyl, naphthyl, substituted phenyl or substituted naphthyl, substituted phenyl or substituted naphthyl and n is an integer from 3 to 6, to form an activated reaction mixture containing substantial amounts of the olefin described above.

24. A process as in claim 23 wherein X is bromo.

25. A process as in claim 23 where the cyclic ligand has the formula set forth above and R' is the same or different than R" and is alkyl having from 1 to 3 carbons and Ar is phenyl and n is an integer from 3 to 6.

26. A process as in claim 25 wherein n is 4.

27. A process as in claim 25 wherein R' is methyl and R" is isopropyl.

28. A process as in claim 25 wherein palladium has a valence of 2.

29. A process as in claim 23 including the additional step of isolating the olefin.

30. A process as in claim 23 including the additional step of converting the olefin to ibuprofen or an ester or salt thereof by reaction with CO.

31. A process as in claim 30 wherein the ester is prepared such that $R_1$ has from 1 to 6 carbon atoms and is hydrolyzed to the corresponding acid in acidic media.

32. A process as in claim 30 wherein the ester is prepared such that $R_1$ has from 1 to 6 carbon atoms and is hydrolyzed in basic media to form a pharmaceutically acceptable salt of ibuprofen wherein the cation is sodium, potassium, calcium, hydrogen carbonate or quaternary ammonium.

33. A process for preparing an aryl-substituted olefin having the formula

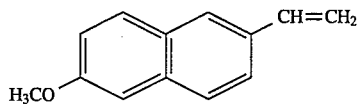

which comprises (i) reacting an aromatic halide of the formula A-X where X is chloro, bromo, iodo, or diazonium and A is 2-bromo-6-methoxynaphthalene with ethylene in the presence of a catalytically effective amount of palladium or the salts of palladium, where palladium has a valence of 1 or 2 and a cyclic ligand of the formula

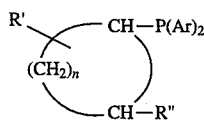

where R' is the same or different than R" and is hydrogen, alkyl or aryl either substituted or unsubstituted and Ar is phenyl, naphthyl, substituted phenyl or substituted naphthyl, substituted phenyl or substituted naphthyl and n is an integer from 3 to 6, to form an activated reaction mixture containing substantial amounts of the olefin described above.

34. A process as in claim 33 wherein X is bromo.

35. A process as in claim 33 where the cyclic ligand has the formula set forth above and R' is the same or different than R" and is alkyl having from 1 to 3 carbons and Ar is phenyl and n is an integer from 3 to 6.

36. A process as in claim 35 wherein n is 4.

37. A process as in claim 35 wherein R' is methyl and R" is isopropyl.

38. A process as in claim 35 wherein palladium has a valence of 2.

39. A process as in claim 33 including the additional step of isolating the olefin.

40. A process as in claim 33 including the additional step of converting the olefin to 2-(6-methoxy-2-naphthyl)propionic acid or an ester or salt thereof by reaction with CO.

41. A process as in claim 40 wherein the ester is prepared such that $R_1$ has from 1 to 6 carbon atoms and is hydrolyzed to the corresponding acid in acidic media.

42. A process as in claim 40 wherein the ester is prepared such that $R_1$ has from 1 to 6 carbon atoms and is hydrolyzed in basic media to form a pharmaceutically acceptable salt of naproxen wherein the cation is sodium, potassium, calcium, or quaternary ammonium.

43. A process for preparing an aryl-substituted olefin having the formula

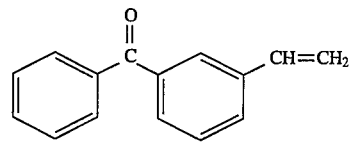

which comprises (i) reacting an aromatic halide of the formula A-X where X is chloro, bromo, iodo, or diazonium and A is 3-benzoyl-1-bromobenzene with ethylene in the presence of a catalytically effective amount of palladium or the salts of palladium, where palladium has a valence of 1 or 2 and a cyclic ligand of the formula

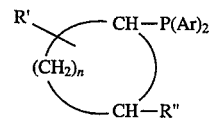

where R' is the same or different than R" and is hydrogen, alkyl or aryl either substituted or unsubstituted and Ar is phenyl, naphthyl, substituted phenyl or substituted naphthyl, substituted phenyl or substituted naphthyl and n is an integer from 3 to 6, to form an activated reaction mixture containing substantial amounts of the olefin described above.

44. A process as in claim 43 wherein X is bromo.

45. A process as in claim 43 where the cyclic ligand has the formula set forth above and $R_1$ is the same or different than R" and is alkyl having from 1 to 3 carbons and Ar is phenyl and n is an integer from 3 to 6.

46. A process as in claim 45 wherein n is 4.

47. A process as in claim 45 wherein R' is methyl and R" is isopropyl.

48. A process as in claim 45 wherein palladium has a valence of 2.

49. A process as in claim 43 including the additional step of isolating the olefin.

50. A process as in claim 43 including the additional step of converting the olefin to ketoprofen or an ester or salt thereof by reaction with CO.

51. A process as in claim 50 wherein the ester is prepared such that $R_1$ has from 1 to 6 carbon atoms and is hydrolyzed to the corresponding acid in acidic media.

52. A process as in claim 50 wherein the ester is prepared such that $R_1$ has from 1 to 6 carbon atoms and is hydrolyzed in basic media to form a pharmaceutically acceptable salt of ketoprofen wherein the cation is sodium, potassium, calcium, or quaternary ammonium.

53. A process for preparing an aryl-substituted olefin having the formula

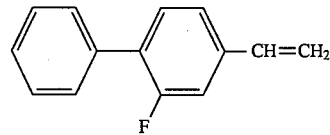

which comprises (i) reacting an aromatic halide of the formula A-X where X is chloro, bromo, iodo, or diazonium and A is 4-phenyl-3-fluoro-1-bromobenzene with ethylene in the presence of a catalytically effective amount of palladium or the salts of palladium, where palladium has a valence of 1 or 2 and a cyclic ligand of the formula

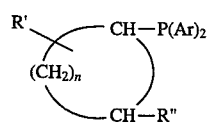

where R' is the same or different than R" and is hydrogen, alkyl or aryl either substituted or unsubstituted and Ar is phenyl, naphthyl, substituted phenyl or substituted naphthyl, substituted phenyl or substituted naphthyl and n is an integer from 3 to 6, to form an activated reaction mixture containing substantial amounts of the olefin described above.

54. A process as in claim 53 wherein X is bromo.

55. A process as in claim 53 where the cyclic ligand has the formula set forth above and R' is the same or different than R" and is alkyl having from 1 to 3 carbons and Ar is phenyl and n is an integer from 3 to 6.

56. A process as in claim 55 wherein n is 4.

57. A process as in claim 55 wherein R' is methyl and R" is isopropyl.

58. A process as in claim 55 wherein palladium has a valence of 2.

59. A process as in claim 53 including the additional step of isolating the olefin.

60. A process as in claim 53 including the additional step of converting the olefin to flurbiprofen or an ester or salt thereof by reaction with CO.

61. A process as in claim 60 wherein the ester is prepared such that $R_1$ has from 1 to 6 carbon atoms and is hydrolyzed to the corresponding acid in acidic media.

62. A process as in claim 53 wherein the ester is prepared such that $R_1$ has from 1 to 6 carbon atoms and is hydrolyzed in basic media to form a pharmaceutically acceptable salt of flurbiprofen wherein the cation is sodium, potassium, calcium, or quaternary ammonium.

* * * * *